United States Patent [19]

Boich

[11] 4,240,416
[45] Dec. 23, 1980

[54] ABSORBENT STRUCTURE

[75] Inventor: Heinz-Horst Boich, Ilsede, Fed. Rep. of Germany

[73] Assignee: J. H. Benecke GmbH, Hanover, Fed. Rep. of Germany

[21] Appl. No.: 907,727

[22] Filed: May 19, 1978

[30] Foreign Application Priority Data

May 20, 1977 [DE] Fed. Rep. of Germany ....... 2722860

[51] Int. Cl.³ .............................................. A61L 15/00
[52] U.S. Cl. .................................. 128/156; 428/236;
128/287; 128/290 R
[58] Field of Search ................. 128/284, 287, 290 R,
128/290 W, 296, 156; 428/236, 245, 296;
8/115.6

[56] References Cited

U.S. PATENT DOCUMENTS

| 2,845,070 | 7/1958 | Lewing | 128/285 |
|---|---|---|---|
| 3,336,923 | 8/1967 | Devaud | 128/296 |
| 3,703,897 | 11/1972 | Mack et al. | 128/156 |
| 3,709,221 | 1/1973 | Riely | 128/156 |
| 3,886,942 | 6/1975 | Bernardin | 128/296 |
| 3,967,623 | 7/1976 | Butterworth et al. | 128/287 |
| 4,077,410 | 3/1978 | Butterworth et al. | 128/287 |

*Primary Examiner*—C. Fred Rosenbaum
*Attorney, Agent, or Firm*—Schwartz, Jeffery, Schwaab, Mack, Blumenthal & Koch

[57] ABSTRACT

A composite flat structure having a high degree of absorption for medical and hygiene purposes, the structure comprising at least two layers having differing moisture absorption characteristics. One of the layers is a cover layer comprised of a composite synthetic bonding agent-free non-woven fibre and another of the layers is a storage layer located below the cover layer. The storage layer has a higher degree of moisture absorption than the cover layer which has such a degree of moisture absorption that, after adaptation to normal climate in accordance with DIN 53 802, it has a moisture content of less than 6% relative to its dry weight in accordance with DIN 53 800. The surface of the fibres of the cover layer is capable of being wetted by the liquids to be absorbed.

4 Claims, 4 Drawing Figures

ABSORBENT STRUCTURE

The present invention relates to a compound flat structure which is highly absorbent. The chief intended use of such a structure is as a dressing for medical or hygiene purposes, but such a structure could also be used for other purposes such as, for example, a lining material for garments.

Flat structures for such purposes are known and their purpose is to absorb liquid body secretions, such as sweat, secretions from wounds, blood and urine, and to store the liquids they absorb. In general, such known structures comprise a highly absorbent storage layer and a cover layer which covers or envelops the storage layer.

In known structures, the cover layer is, usually, also highly absorbent. Although such a structure provides good liquid storage, the liquids are constantly in direct contact with the human skin, causing skin irritation and inflammation.

It has therefore been suggested to overcome this problem by using a less absorbent fibrous material for the cover layer facing the skin. To achieve this, the cover layer is treated with a water repellent agent and the storage layer with a wetting agent. In another known structure, a "dampness absorbing device" includes a cover layer having a moisture absorption capacity of not more than 0.5%. In such a case, the cover layer is made exclusively of polypropylene fibres which, as is known, are highly water repellent per se.

Practice, however, has shown that such a known two-ply flat structure does not function entirely successfully. The water repellent cover layer did not provide a pleasant, dry touch to the skin and directly prevented the body secretions to pass quickly and completely into the storage layer and so did not permit the skin to be kept dry, which was of particular importance if the dressing was being used to cover a wound.

The present invention therefore seeks to provide an absorbent flat structure in which the liquids secreted from the human body are quickly and completely removed from the skin and are stored away from contact with the skin.

According to the present invention there is provided a composite flat structure having a high degree of absorption for medical and hygiene purposes, the structure comprising at least two layers having differing moisture absorption characteristics, one of the layers being a cover layer comprised of a composite synthetic bonding agent-free non-woven fibre, and another of the layers being a storage layer located below the cover layer, the storage layer having a higher degree of moisture absorption than the cover layer wherein the cover layer has such a degree of moisture absorption which is such that, after adaptation to normal climate in accordance with DIN 53 802, it has a moisture content of less than 6% relative to its dry weight in accordance with DIN 53 800, and wherein the surface of the fibres of the cover layer is capable of being wetted by the liquids to be absorbed. The above referred to DIN designations constitute German industry standards which are well known to those skilled in the art. The DIN designations correspond to U.S. industry standards ASTM D 2654 and ASTM D 1776, respectively.

Surprisingly, by providing such an arrangement and not a water repellent cover layer, optimum conditions for drying the skin or a wound are achieved, even though the layer in contact with the skin is comprised of wettable fibres. By providing a cover layer which is capable of being wetted and has slight moisture absorbency, the cover layer simultaneously constitutes a conveying medium and a barrier for the liquids to be absorbed by the storage layer. Since it is capable of being wetted, the liquids can find their way through the cover layer into the storage layer without interruption and, since the cover layer has only a low degree of absorption, substantially all of the liquid is transferred immediately into the storage layer. The cover layer therefore remains substantially dry. It appears to be a combination of the moisture absorbancy characteristics and the capacity of the cover layer to be wetted which produces the desired effect.

The cover layer is preferably comprised of water-repellent fibres, such as, for example, endlessly spun composite, bonding agent-free polypropylene fibres laid in random non-woven fibre form, the surface of which is made capable of being wetted by the application of a wetting agent. The wetting agent is preferably present in an amount of from 0.1 to 10 mg wetting agent per gram of fibre weight. The weight of suitable non-woven fibres is generally below 50 g/m$^2$ and the fibre denier is generally less than 3 denier. The reaction product of castor oil and ethylene oxide reacted in a molar ratio of substantially 1:40 has proved to be particularly suitable for use as the wetting agent.

To prevent the storage layer from discharging the moisture absorbed on its free rear surface, it is desirable if this surface is covered with a moisture-repellent, air-permeable barrier layer. This barrier layer is preferably made of a material which differs only from the material of the cover layer in that it is not treated with a wetting agent.

The present invention also relates to a method of producing such a structure wherein a web of composite moisture-repellent, bonding agent-free synthetic non-woven fibre is provided with a fibrous storage layer having a high moisture storage capacity by locating the storage layer on the cover layer and folding the cover layer around the storage layer, the free ends of the cover layer then being interconnected so as to envelop the storage layer, the cover layer then being treated with a wetting agent only on the side thereof to be applied to the skin.

The invention will be further described, by way of example, with reference to the accompanying drawing, in which.

Figure 1:
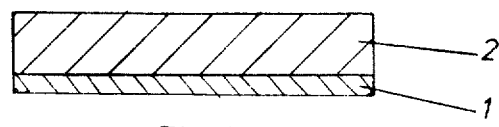
FIG. 1 shows a basic embodiment of a structure in accordance with the present invention.
Figure 2:
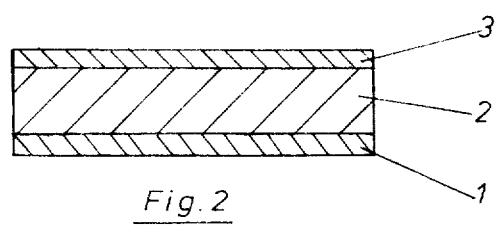
FIG. 2 shows a modified structure having an additional barrier layers.

In FIG. 1, there is shown an absorbent cover layer 2, to one surface of which is applied a cover layer 1. The cover layer 1 is made of water repellent, bonding agent-free fibres which are treated with a wetting agent so that the cover layer can be wetted by the fluid to be absorbed. In the embodiment shown in FIG. 2, a barrier layer 3 is provided on the surface of the absorbent layer 2 remote from the cover layer 1. The barrier layer 3 is made of the same material as the cover layer 1 but is not treated with a wetting agent.

Figure 3:
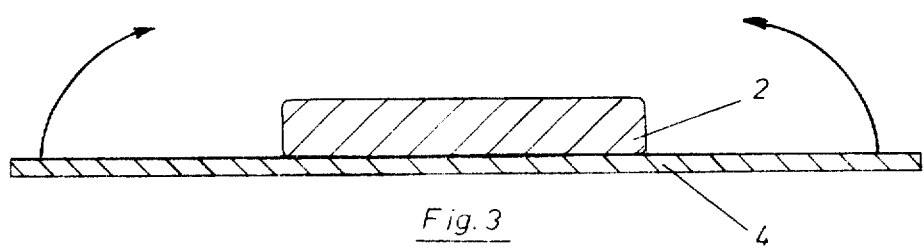
FIGS. 3 and 4 show various stages in a process for manufacturing the structure of FIG. 2.
Figure 4:
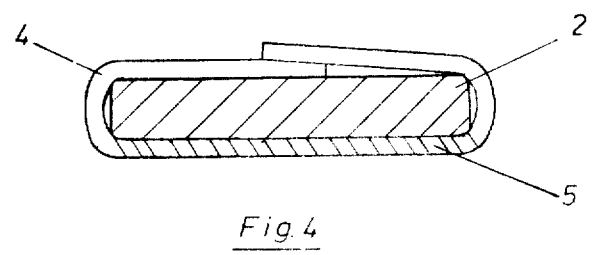

In FIGS. 3 and 4, there are shown two stages in the preparation of such a structure. As shown in FIG. 3, a storage layer 2 is located on a moisture repellent non-woven fibre layer 4 which is intended to become the cover layer 1. The fiber layer 4 is considerably longer than the layer 2. The ends of the fibre layer 4 are then folded in the direction of the arrows to form the structure shown in FIG. 4. The ends of the layer 4 are then interconnected and one surface 5 of the layer is treated with a wetting agent.

Besides the preferred arrangement of treating the storage layer with a wetting agent, the present invention also includes the possibility of utilising other methods to produce a fibre surface capable of being wetted. For example, in this sense, treatment with a coronal discharge may be considered.

What we claim is:

1. A composite flat structure having a high absorption capacity for medical and hygiene purposes, the structure comprising at least two layers having differing moisture absorption characteristics, one of the layers being a cover layer comprised of non-woven bonding agent-free bonded synthetic fibres and another of the layers being a storage layer located below the cover layer, the storage layer having a higher moisture absorption capacity than the cover layer, said cover layer being treated with a wetting agent and having a moisture absorption capacity such that, after adaptation to normal climate in accordance with DIN 53 802, it has a moisture content of less than 6% relative to its dry weight in accordance with DIN 53 800, and wherein the surface of the fibres of the cover layer treated with the wetting agent is capable of being wetted by the liquids to be absorbed and to pass such liquids without interruption to said storage layer so that said cover layer remains dry to the skin, said cover layer comprising moisture repellent fibres, the surfaces of which are treated with said wetting agent, and wherein said wetting agent comprises a reaction product of castor oil and ethylene oxide reacted in a molar ratio of substantially 1:40.

2. A structure as claimed in claim 1, wherein the wetting agent for the cover layer is present in an amount of from 0.1 to 10 mg per gram of fibre weight.

3. A composite flat structure having a high absorption capacity for medical and hygiene purposes, the structure comprising at least two layers having differing moisture absorption characteristics, one of the layers being a cover layer comprised of non-woven bonding agent-free bonded synthetic fibres and another of the layers being a storage layer located below the cover layer, the storage layer having a higher moisture absorption capacity than the cover layer, said cover layer being treated with a wetting agent and having a moisture absorption capacity such that, after adaptation to normal climate in accordance with DIN 53 802, it has a moisture content of less than 6% relative to its dry weight in accordance with DIN 53 800, and wherein the surface of the fibres of the cover layer treated with the wetting agent is capable of being wetted by the liquids to be absorbed and to pass such liquids without interruption to said storage layer so that said cover layer remains dry to the skin, the rear surface of said storage layer remote from said cover layer being provided with a moisture repellent, air-permeable barrier layer, said barrier layer being formed of the same material as the cover layer with the exception that it is not treated with a wetting agent.

4. A method of manufacturing a composite structure having a high degree of absorption and including a web of composite moisture repellent, bonding agent-free synthetic non-woven fibre and a fibrous storage layer having a high moisture storage capacity, comprising the steps of locating the storage layer on the cover layer and folding the cover layer around the storage layer, interconnecting the free ends of the cover layer so as to envelop the storage layer, and treating said cover layer with a wetting agent only on the side thereof to be applied to the skin.

* * * * *